United States Patent [19]

Coleman

[11] Patent Number: 5,591,207
[45] Date of Patent: Jan. 7, 1997

[54] DRIVING SYSTEM FOR INSERTING THREADED SUTURE ANCHORS

[75] Inventor: R. Glen Coleman, Clearwater, Fla.

[73] Assignee: Linvatec Corporation, Largo, Fla.

[21] Appl. No.: 413,568

[22] Filed: Mar. 30, 1995

[51] Int. Cl.$^6$ ............................................. A61B 17/00
[52] U.S. Cl. ...................... 606/232; 606/73; 606/96; 606/104; 81/451
[58] Field of Search ................. 606/232, 73, 65, 606/60, 72, 104, 75, 148, 139, 86, 96, 99, 53; 623/13; 24/453; 81/52, 53.2, 451, 57.13, 57.14

[56] References Cited

U.S. PATENT DOCUMENTS

| | | |
|---|---|---|
| 734,204 | 7/1903 | Voss ............................................ 81/451 |
| 3,892,232 | 7/1975 | Neufeld ...................................... 606/96 |
| 4,710,075 | 12/1987 | Davison ................................... 408/202 |
| 4,898,156 | 2/1990 | Gatturna et al. . |
| 4,899,743 | 2/1990 | Nicholson et al. . |
| 4,946,468 | 8/1990 | Li . |
| 4,968,315 | 11/1990 | Gatturna . |
| 5,046,513 | 9/1991 | Gatturna et al. . |
| 5,100,417 | 3/1992 | Cerier et al. . |
| 5,102,421 | 4/1992 | Anspach, Jr. . |
| 5,141,520 | 8/1992 | Goble et al. . |
| 5,192,303 | 3/1993 | Gatturna et al. . |
| 5,207,679 | 5/1993 | Li . |
| 5,217,486 | 6/1993 | Rice et al. . |
| 5,224,946 | 7/1993 | Hayhurst et al. . |
| 5,258,016 | 11/1993 | Di Poto et al. . |
| 5,261,914 | 11/1993 | Warren . |
| 5,358,511 | 10/1994 | Gatturna et al. . |
| 5,370,662 | 12/1994 | Stone et al. ................................ 606/73 |
| 5,411,506 | 5/1995 | Goble et al. . |
| 5,411,523 | 5/1995 | Goble . |
| 5,466,243 | 11/1995 | Schmieding et al. ................... 606/232 |

OTHER PUBLICATIONS

Linvatec Product Sheet, Rotator Cuff Repair with a New Twist, 1993, 2 Pages.
Linvatec Product Catalog, The Revo Rotator Cuff Fixation System, Surgical Technique, 1993, 8 Pages.

*Primary Examiner*—Michael Powell Buiz
*Assistant Examiner*—Jeffrey A. Schmidt
*Attorney, Agent, or Firm*—Gene Warzecha

[57] ABSTRACT

A driving system and method for endoscopically inserting threaded suture anchors. The driving system incorporates a tubular guide adapted to receive a cylindrical drive shaft having a drive portion at its distal tip for engaging a threaded anchor and a stop member at its proximal end for enabling rotational motion of the drive system relative to the drill guide while limiting longitudinal motion beyond a predetermined point. The stop member is, in the preferred embodiment, an annular shoulder which prevents the drive shaft from advancing the anchor into the bone more than a desired amount sufficient to countersink the anchor below the bone surface. The invention facilitates use of a drive shaft having a minimized shaft diameter. The invention also comprises a method of using the driving system, the method comprising the steps of both turning and longitudinally limiting the motion of the driver from the proximal side of the driver. An additional invention disclosed comprises a method of threading a suture through an anchor after the anchor has been implanted by a drive shaft having a minimized shaft diameter.

2 Claims, 4 Drawing Sheets

DRIVING SYSTEM FOR INSERTING THREADED SUTURE ANCHORS

BACKGROUND OF THE INVENTION

1. Field of the Invention

The invention relates to anchors for attaching soft tissue to bone. More particularly, the invention relates to apparatus and methods related to inserting suture anchors in bone in order to attach soft tissue thereto.

2. Description of the Prior Art

In the course of certain surgical procedures, soft tissue is secured to a selected bone surface either directly, via some type of implant, or indirectly via an implant (i.e. an anchor) to which suture is attached, the suture then being tied to the soft tissue to hold it in place. Anchors may be used to attach soft tissue such as ligaments, tendons, muscles, etc. to a surface from which the soft tissue has become detached and may also be used to secure soft tissue to supplementary attachment sites for reinforcement. For example, in urological applications anchors may be used in bladder neck suspensions to attach a portion of the bladder to an adjacent bone surface. Such soft tissue attachment may be done during either open or closed surgical procedures, the latter being generally referred to as arthroscopic or endoscopic surgery. The terms "arthroscopic" and "endoscopic" may be used interchangeably herein and are intended to encompass arthroscopic, endoscopic, laparoscopic, hysteroscopic or any other similar surgical procedures performed with elongated instruments inserted through small openings in the body.

In procedures requiring suturing of soft tissue to bone, the suture may either be first anchored by so-called suture anchors to the bone before passing the suture through the soft tissue, or the tissue may first be sutured and the anchor may then be slid down one leg of the suture and then implanted into bone. The prior art includes numerous types of suture anchors adapted to be secured in the bone, sometimes directly in one step and sometimes in pre-drilled holes or tunnels. The term "suture anchor" is used broadly and will be understood to refer to devices having a similar structure even if material other than suture is connected to the device. Some prior art suture anchors are elongated and have annular ribs or radially extending barbs and are required to be pushed or hammered directly into bone or into a preformed bone tunnel (exemplified by U.S. Pat. Nos. 5,102,421 (Anspach, Jr.); 5,141,520 (Goble et al.); 5,100,417 (Cerier et al.); 5,224,946 (Hayhurst et al.) and 5,261,914 (Warren)). Pushing an anchor into place has the disadvantage of potential trauma and damage to surrounding bone tissue, and has limited applicability where the location of the bone tunnel or pre-drilled hole is not axially aligned with an arthroscopic portal to permit transmission of the impacting force through an impactor to the anchor. An impacted suture anchor is not easily removable without damaging the bone into which it has been placed. Consequently, threaded suture anchors are often used as exemplified by U.S. Pat. Nos. 5,156,616 (Meadows et al.) and 4,632,100 (Somers et al.). Depending upon the type of threaded anchor, the insertion procedure may enable direct threading of the anchor into the bone or it may sometimes require that a pilot hole first be drilled into the bone, the hole then either enabling an anchor to be screwed in or enabling threads to be tapped to receive the anchor.

Devices used to insert suture anchors into bone surfaces provide an interface between the actual implant and the surgeon performing the procedure. While this interface is most important in endoscopic surgical procedures because of the limited accessibility of the surgical site, prior art endoscopic procedures generally utilize devices and methods designed for open surgical procedures. All known procedures used to insert suture anchors endoscopically rely on elongated extensions which pass through the portals or cannulas used in the procedures. Similar elongated extensions are also used in open procedures. With respect to non-threaded or non-turnable suture anchors, these extensions merely are required to transmit longitudinal forces from the proximal end to the distal end where the suture anchor is situated. With respect to turnable or threaded suture anchors, the inserting device must be elongated as well as strong enough to transmit sufficient torque from the proximal end to the distal tip to turn the anchor.

Threaded suture anchors are preferably inserted into the bone surface so that the proximal end of the anchor lies at or beneath the bone surface in order not to injure the soft tissue which is intended to be approximated to the bone surface. Consequently, the inserting device must be able to countersink the anchor a sufficient degree. Furthermore, known suture anchors are inserted with the suture already joined to the anchor so the anchor driver must, therefore, accommodate suture while it is turning.

A known threaded anchor inserting device is used to drive a threaded anchor of the type shown in aforementioned U.S. Pat. No. 4,632,100 (Somers et al.), incorporated herein by reference. The anchor is known as the STATAK™ soft tissue attachment device, available from the assignee hereof, and is premounted with suture in a disposable driver which fits any standard cannulated drill. The driver is an elongated hollow tube having a drive recess at its distal end for engaging a corresponding drive surface on the anchor (FIG. 1). The driver has an annular shoulder near its distal end, proximal to the drive recess in order to abut the bone surface at the site of implantation of the anchor. When the driver is turned, the threaded anchor advances into the bone (FIGS. 2 and 3) and, after the shoulder abuts the bone, the driver continues to turn to advance the anchor further to assure that its proximal end becomes countersunk (FIG. 4). The driver includes an automatic release feature to disengage from the anchor when it is properly positioned. This feature causes the anchor to automatically stop advancing and turning when it reaches a predetermined depth below the bone surface, that depth being defined at the point where its driver portion advances beyond the distal tip of the driver. Removal of the driver deploys the suture which was arrayed inside.

While in open procedures the anchor and driver assembly may be directly used as described above, in endoscopic procedures the anchor and driver assembly must first be inserted through a portal or cannula to position the anchor at the implantation site. Preferably, a cannula is used to avoid injuring tissue with the anchor. The internal diameter of the cannula must be large enough to pass the driver. The shoulder at the distal end of the driver necessitates the use of a large diameter cannula. Furthermore, in order to minimize trauma to the patient and facilitate the use of suture anchors at certain sites, a cannulated drill guide is necessary to hold the driver in place as it is turned. Using such a drill guide in addition to the known driver necessitates the use of a still larger cannula in order to enable the suture anchor to be properly used endoscopically. Because of the limited visibility available in endoscopic procedures, it is always desirable to minimize the size of the instrumentation as much as possible. This decrease in size improves visualization and enables the use of endoscopic instruments in small confined spaces. It would be desirable to produce a smaller diameter driver than presently known so that smaller cannulae could be used to minimize the size of the required portal and also to facilitate anchor use in certain small, confined locations (shoulder, etc.).

Additionally, insertion of threaded suture anchors in some situations may be improved if the anchor could be inserted to varying depths. It would be desirable, therefore, to produce a driver capable of inserting an anchor to different depths.

Prior art anchor drivers of the type having a distal shoulder are only suitable for driving the threaded anchor into place. Once the anchor advances beyond the tip of the drive shaft, the anchor is no longer reachable with the driver and, if one desires to remove the anchor, a separate instrument must be used. It may in some instances be desirable to remove the anchor and having a driver which could serve as a remover could be helpful in certain situations.

It is accordingly an object of this invention to produce a system for inserting threaded suture anchors.

It is also an object of this invention to produce a driving system capable of countersinking a threaded suture anchor while minimizing the diameter of the driver.

It is another object of this invention to produce a driving system capable of countersinking a threaded suture anchor to varying depths.

It is an additional object of this invention to produce a driving system for inserting threaded suture anchors which is smaller than known systems in order to improve visualization and provide greater access to confined spaces.

It is also an object of this invention to produce a driver which can also be used for removal of a threaded suture anchor while also enabling countersinking of the suture anchor upon insertion.

SUMMARY OF THE INVENTION

These and other objects of this invention are achieved by the preferred embodiment disclosed herein which comprises a driver system for inserting a threaded bone anchor having a cylindrical body provided with a threaded external surface, a driver-receiving portion for engaging a driver and a suture-receiving portion for engaging a suture. The driver system comprises a tubular drill guide provided with a cylindrical axial bore having a predetermined diameter and a predetermined length and a tubular drive shaft having a distal end and a proximal end. The distal end of the drive shaft has an automatically releasable drive means for engaging the driver-receiving portion of the anchor and releasing the anchor when it reaches a predetermined depth. The tubular drive shaft has an outer diameter smaller than that of the drill guide interior to enable the drive shaft to pass through the drill guide. A stop means is affixed to the drive shaft at a predetermined distance from its distal end, this distance being greater than the length of the drill guide. The stop means enables the drive shaft to rotate relative to the drill guide while preventing the drive shaft from moving longitudinally relative to the drill guide beyond a predetermined point.

The invention also comprises a method of inserting a threaded bone anchor. The method comprises the steps of providing a tubular drill guide provided with a cylindrical axial bore having a predetermined diameter and a predetermined length, and providing a tubular drive shaft having a distal end and a proximal end. The distal end of the drive shaft has an automatically releasable drive means for engaging the threaded anchor and the body of the drive shaft has an outer diameter smaller than the predetermined diameter to enable the drive shaft to pass through the drill guide. The method further comprises the steps of assembling the anchor onto the distal end of the drive shaft; placing the distal end of the drill guide at a selected site targeted to receive the anchor and inserting the drive shaft and anchor assembly into the proximal end of the drill guide. The method also comprises the steps of providing a stop means at the proximal end of the drive shaft and turning the drive shaft to advance the anchor into the selected site to abut the stop means against the proximal end of the drill guide.

In another aspect of the invention, the method includes the threading of suture through the anchor after its implantation and additionally comprises the steps of threading through the anchor eyelet a "threading suture" which is sufficiently small in diameter to enable both ends of the suture to extend from one side of the eyelet while the central or bight portion of the suture extends from the other side of the eyelet to create a loop. The "holding suture" actually used to hold tissue to the anchor is then passed through the tissue and one leg of this suture is passed through the "threading suture" loop. Pulling the ends of the "threading suture" causes one leg of the "holding suture" to pass through the anchor eyelet. The legs of the "holding suture" may then be tied in a conventional manner.

DESCRIPTION OF THE PREFERRED EMBODIMENT

The present invention will be better understood by reference to a prior art device used to insert threaded suture anchors. As mentioned above, FIGS. 1 through 4 show a prior art STATAK™ driver and some of the steps in using the driver to insert the STATAK™ threaded suture anchor at a site of implantation.

Figure 1:
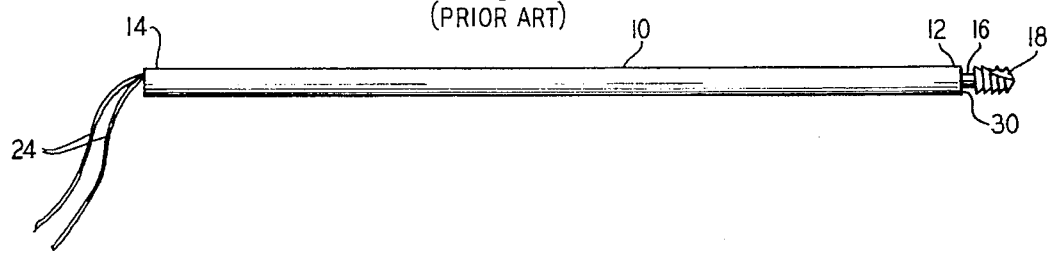
FIG. 1 shows a side elevation view of a prior art threaded suture anchor assembled with a driver.

The STATAK™ driver 10 is a hollow tube having a distal end 12 and a proximal end 14. Distal end 12 is provided with a drive recess portion 16 into which the proximal end of a STATAK™ suture anchor 18 is inserted. As will be best seen in FIG. 4, anchor 18 has at its proximal end a drive portion 20 and an eyelet 22 for receiving a suture 24. The drive recess has a non-circular bore adapted to engage a similarly shaped drive portion of anchor 18. Alternatively, the drive recess can engage the eyelet portion of the implant and turn the implant by using the eyelet portion as a non-circular drive portion. Suture 24 is placed within the interior of driver 10 and may extend proximally from the proximal end 14 as shown in FIG. 1. The suture is tied to or threaded through the eyelet 22 so that two ends of suture 24 may extend from the proximal end of driver 10. In actuality, the two lengths of the suture may be folded on themselves near the proximal end of tube 10 so the suture remains totally within the tube. The proximal end of the tube may be closed with a plug (not shown). The distal end 12 of driver 10 has a shoulder 30 which, although not shown as such, will be understood by reference to FIGS. 2 through 4 to abut the bone surface around the hole formed at the site of implantation.

Figure 2:
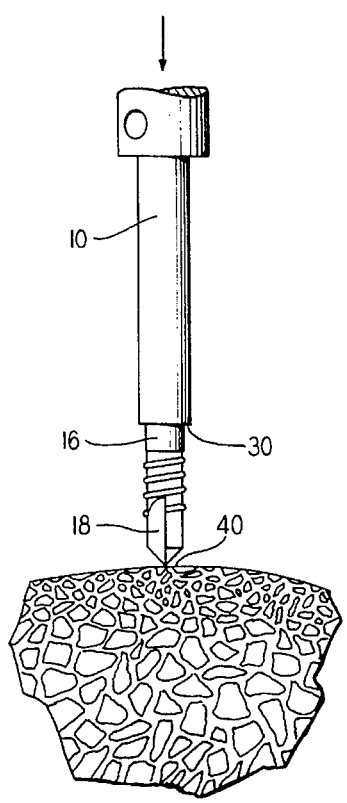
FIG. 2 is a diagrammatic view of the distal end of a driver/anchor assembly of FIG. 1 shown inserted into a drill chuck and situated above an implantation site on a bone surface.
Figure 3:
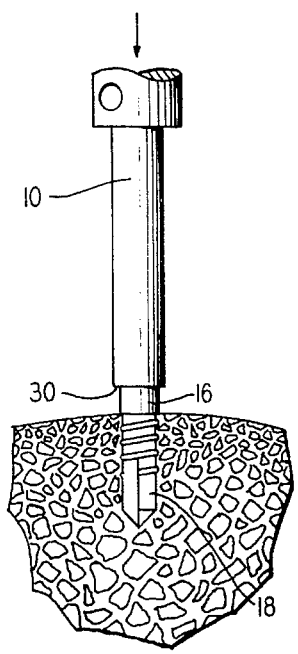
FIG. 3 is a view of FIG. 2 showing the threaded anchor partially advanced into the bone.

Referring now to FIGS. 2 and 3, anchor 18 is shown in position above a site of implantation 40 during an open surgical procedure. Driver 10 is rotated and pushed distally in order to embed anchor 18 into the site of implantation. As the anchor continues advancing distally, the drive recess portion 16 follows the anchor into the drilled hole formed by the anchor, and abutment shoulder 30, being larger in diameter than drive recess 16 abuts the annular surface of the bone immediately adjacent the drilled hole. The shoulder may be radiused into the outer surface of portion 16 (not shown). Further turning of the driver causes anchor 18 to advance to the depth shown in FIG. 4 at which point drive recess 16 no longer engages drive portion 20 because shoulder 30 prevents drive recess 16 from entering further into the hole. At this point, anchor 18 is properly countersunk and the driver 10 may be removed thereby pulling suture 24 from its interior.

Figure 4:
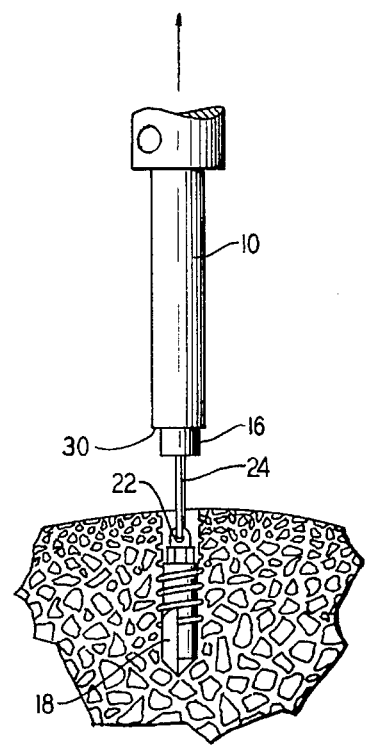
FIG. 4 is a view of FIG. 3 showing the anchor further advanced into the bone and the driver and drill moving a direction away from the implantation site.

While FIGS. 2 through 4 show the use of the prior art driver during an open procedure, a similar procedure could be used endoscopically. However, it is preferable in endoscopic procedures to insert the driver and anchor through a separate cannula which passes through a portal at the surgical site. Such a cannula (best seen in FIG. 7) is helpful to decrease the likelihood of trauma to the tissue created by the sharp edges of the threaded implant. Moreover, some tubular guide is also generally required in endoscopic procedures to assure that the implant and driver are able to be held during implantation. Thus, in endoscopic procedures using a cannula, the internal diameter of the cannula must be large enough to accommodate the outer diameter of any drive shaft used to drive the anchor as well as the guide within which the driver fits. If a driver designed for use in open surgical procedures were to be used in endoscopic procedures, unacceptable part dimensions would result. For example, while the outer diameter of drive shaft 10 varies as a function of the size of the implant, the general range of such diameters is 0.208 inches to 0.250 inches (approximately 5.3–6.4 mm). In order to accommodate these drivers alone, without any tubular guide, the external diameters of the associated cannula, given the necessity for a predetermined amount of cannula wall thickness, must be on the order of 8–10 mm. Adding a tubular guide, even one having a fairly thin wall thickness would add at least 2 mm or more to such a cannula. Such cannula sizes are not normally produced and, even if they were, they would preclude the use of such drivers in certain endoscopic procedures. Common cannula (outer) diameters are on the order of 8 mm to 10 mm having internal diameters of 6 mm to 8.5 mm, respectively. The preferred embodiment of the invention may be made to fit in these cannulae without the need to produce larger sizes which would limit visualization and restrict access to implantation sites.

Figure 5:
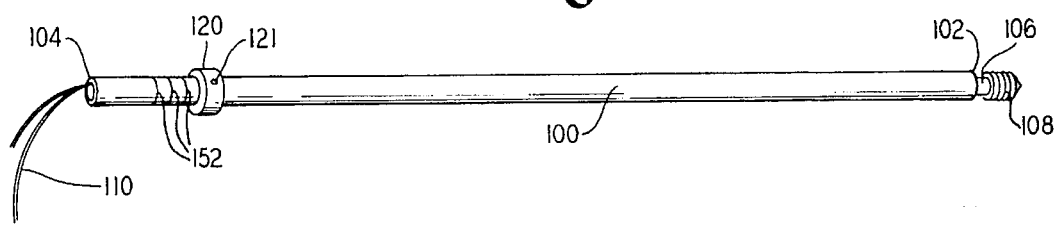
FIG. 5 is a side elevation view in perspective showing a threaded anchor driver constructed in accordance with the principles of this invention.

A threaded anchor driver constructed in accordance with the principles of the invention is shown in FIG. 5 comprising an elongated tubular drive shaft 100 having a distal end 102 and a proximal end 104. Distal end 102 is provided with a drive recess 106 having a cross-section complementary to the drive portion of threaded anchor 108 (identical to previously described threaded anchor 18). Distal end 102 is sized to that it may follow anchor 108 into the hole made by the anchor. That is, there is no stop surface at end 102 since the function of limiting the depth of penetration of the anchor is accomplished differently in the preferred embodiment. In the preferred embodiment, anchor 108 is pre-threaded with suture 110 and inserted in drive recess 106 so that suture 110 either extends from the proximal end 104 as shown or is otherwise coiled, folded or retained in the interior of drive shaft 100 (similar to the manner in which the prior art driver is loaded). For purposes to be described below, drive shaft 100 is provided with a movable annular shoulder stop 120 intermediate ends 102 and 104. The shoulder stop is adjustable along shaft 100 and is fixed thereof by set screw 121.

Figure 6:
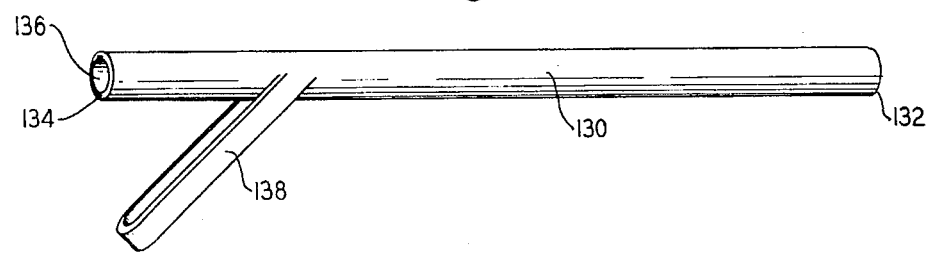
FIG. 6 is a side elevation view in perspective showing a drill guide for use with the threaded anchor driver of FIG. 5.

Drive shaft 100 is used in conjunction with a tubular guide 130 shown in FIG. 6. Both drive shaft 100 and guide 130 are sufficiently elongated to enable their use during endoscopic surgical procedures. Guide 130 has a distal end 132, a proximal end 134 and an internal axial bore 136 having an inside diameter slightly larger than the outside diameter of driver shaft 100. The diameter of driver shaft 100 may be less than or equal to the major diameter of the thread of the anchor. A handle 138 may be provided to manipulate guide 130 as desired.

Figure 7:
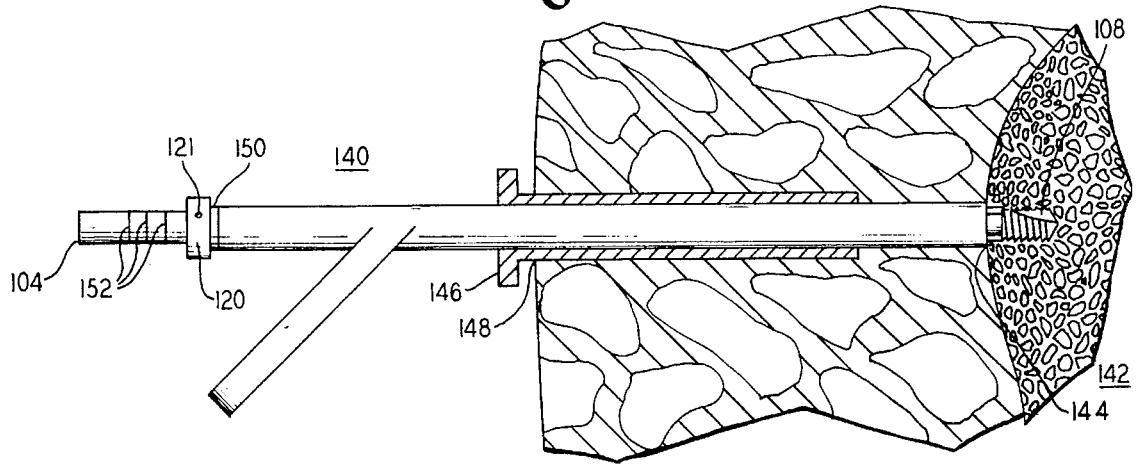
FIG. 7 is a side elevation view of a driver anchor system comprising the assembly of the components of FIGS. 5 and 6 and showing the distal end of the driver system adjacent a bone surface.
Figure 8:
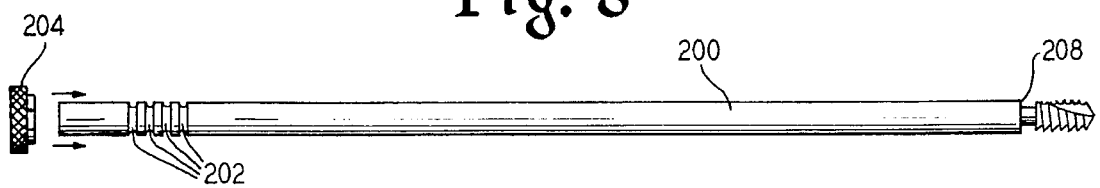
FIG. 8 is a side elevation view of another alternative embodiment of a threaded anchor driver having a movable stop member.
Figure 9:
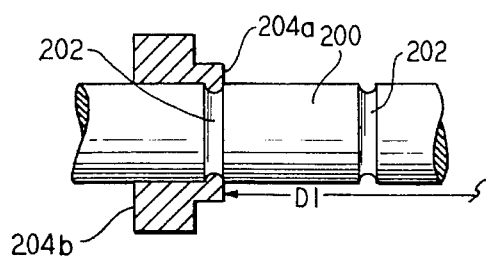
FIGS. 9 and 10 are exploded views of a portion of FIG. 8 showing alternate arrangements of parts.
Figure 10:
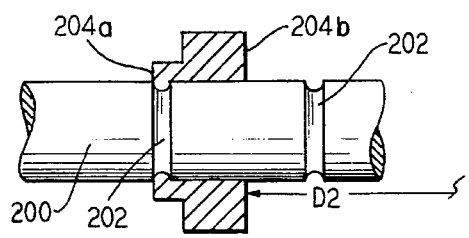
Figure 11:
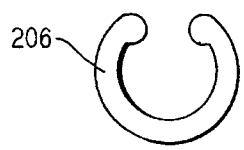
FIG. 11 is a top plan view of an alternate stop member for use with the driver of FIG. 8.

The drive shaft and guide are assembled as shown in FIG. 7 and operate as a drive system 140 to insert anchor 108 into bone 142 at an implantation site 144. The system is inserted through a cannula 146 inserted in a portal 148. A drill or handle (not shown) is attached to proximal end 104 in order to turn anchor 108. As the anchor advances into the bone, shoulder stop 120 approaches the proximal end 134 of guide 130. The lengths of drive shaft 100 and guide 130 are such that when the distal end 132 of guide 130 abuts the implantation site, the distally facing surface 120a of shoulder stop 120, abuts end 134 when the anchor 108 is properly countersunk to a desired depth. To minimize any resistance between the turning of shoulder stop and the stationary guide, a bearing or coating 150 may be provided at proximal end 134 (or on stop surface 120a). Additionally, shoulder stop 120 may be continuously adjustable along the length of drive shaft 100 by tightening set screw 121 as desired to vary the position of stop surface 120a and, therefore, the depth to which anchor 108 can be inserted. Indicia 152 may be provided to facilitate proper placement of the stop on the shaft. In another drive shaft embodiment 200 as shown in FIGS. 8 and 11, discrete depth adjustments are made possible by providing the surface of the drive shaft with longitudinally spaced detent grooves 202 to receive a snap collet 204 or snap ring 206. An additional benefit of snap collet 204 is that it may be reversed so that a stop surface 204a may face distally as shown in FIG. 9 or the other side 204b of collet 204 may be faced distally as shown in FIG. 10. In the configuration of FIG. 9, the distance D1 from distal tip 208 to surface 204a is, therefore, greater than the distance D2 of the configuration shown in FIG. 10. Thus, the mere positioning of collet 204 enables one drive shaft to provide a greater number of choices of depth penetration.

Normally, the outer diameter of drive shaft 100 (or 200) is defined by the diameter of the distal annular edge which abuts the bone. The internal diameter is defined by this outer diameter less a certain necessary wall thickness. In certain embodiments in which suture extending from an anchor is kept totally within the hollow driver, the minimum size of the internal diameter of the drive shaft is constrained by the size of the suture which may be threaded through the anchor and which may be doubled up on itself or otherwise arrayed within the driver. In some embodiments as described above, the suture threaded through the anchor extends into the driver towards its proximal end and then both legs of the suture are doubled back towards the distal end of the driver so that in effect there are four strands of suture within the interior of the driver. This creates a convenient situation for driving the anchor by turning the drive shaft without having any suture extending outside the periphery of the drive shaft. In the preferred embodiment, since a large diameter drive shaft is no longer necessary to limit the depth of implantation of the anchor, the size of the drive shaft may be minimized but for the internal space that must be maintained to accommodate storing the suture in the drive shaft. However, for certain suture sizes the necessity for providing a large internal diameter of the drive shaft to accommodate four suture strands may require such drivers to be undesirably large, especially for endoscopic applications. Additionally, certain types or sizes of suture may be difficult to use in known methods of inserting anchors.

Figure 12A:
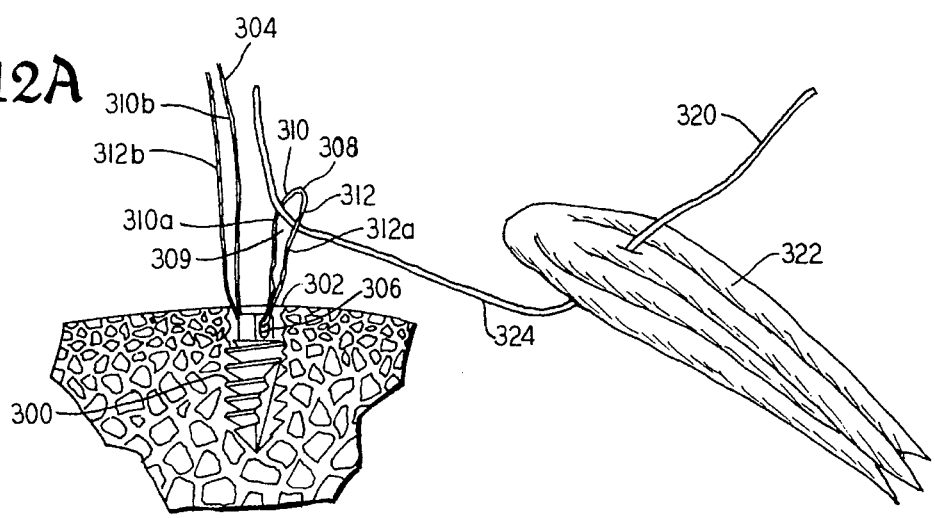
FIGS. 12a, 12b and 12c are sequential diagrammatic views showing some steps of a method of passing suture through the eyelet of a threaded anchor after the anchor has been embedded in bone.
Figure 12B:
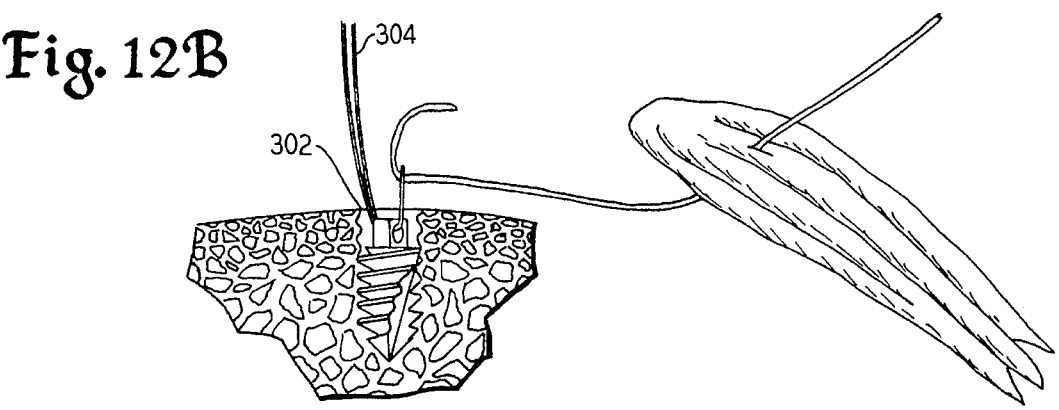
Figure 12C:
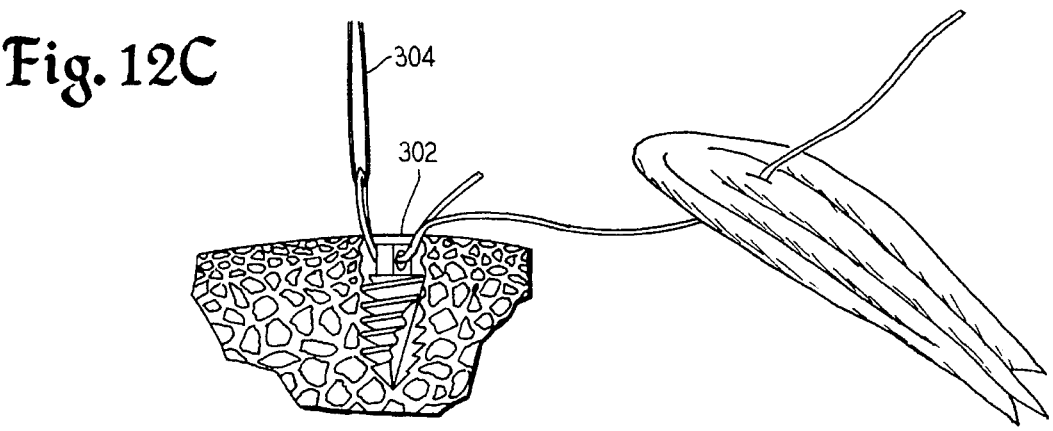

The invention disclosed herein includes an improvement in this method of inserting a threaded anchor by minimizing the size of the driver required for any given suture size. As shown in FIGS. 12a, 12b and 12c, threaded anchor 300 is inserted at an implantation site 302 with a doubled up length of temporary "threading" suture 304 already in place in the eyelet 306 of the anchor. Threading suture 304 is folded about its center point or bight 308 to produce a loop 309 and legs 310 and 312. Suture leg 310 comprises a proximal portion 310a extending from central point 308 toward the anchor and a portion 310b extending from the anchor. Suture leg 312 similarly comprises a proximal portion 312a extending from the central point 308 to the anchor and a distal portion 312b extending from the anchor. The diameter of threading suture 304 is sufficiently small so that the two strands 310 and 312 may pass through the eyelet 306 while four strands 310a, 310b, 312a and 312b may pass through the internal diameter of the drive shaft (not shown).

A permanent "holding suture" 320 is passed through tissue 322 in order to enable the tissue ultimately to be connected to anchor 300. A surgeon may select a variety of suture styles and sizes by using a temporary suture to thread a permanent suture as shown. Therefore, the temporary suture/anchor assembly could be uniformly assembled while enabling a great variety of final suture/anchor configurations. The diameter of holding suture 320 would generally be greater than that of threading suture 304 and one end 324 of suture 320 is passed through loop 309 of threading suture 304 and pulled through eyelet 306 as best seen in FIGS. 12b and 12c. The permanent suture can then be tied in a conventional manner.

It will be understood by those skilled in the art that numerous improvements and modifications may be made to the preferred embodiments of the invention disclosed herein without departing from the spirit and scope thereof.

What is claimed is:

1. A driver system for inserting a threaded bone anchor, said anchor having a cylindrical body provided with a threaded external surface, a driver-receiving portion for engaging a driver and a suture-receiving portion for engaging a suture, said driver system comprising:

a tubular guide provided with a cylindrical axial bore having a predetermined diameter and a predetermined length:

a tubular drive shaft rotatable within and relative to said tubular guide said drive shaft having a distal end and a proximal end, said distal end having an automatically releasable drive means for engaging said driver-receiving portion of said anchor, said tubular drive shaft having an outer diameter smaller than said predetermined diameter to enable said drive shaft to pass through said guide;

a stop means affixed to said drive shaft at a predetermined distance from said distal end thereof, said predetermined distance greater than said predetermined length said stop means preventing said drive shaft from moving longitudinally relative to said guide beyond a predetermined point while enabling said drive shaft to rotate relative to said guide and to be removed therefrom; and bearing means interposed between said stop means and said guide for facilitating the contiguous rotation of said stop means relative to said guide.

2. A method of inserting a threaded bone anchor, having an eyelet for receiving suture, at an implantation site comprising the steps of:

turning, with an elongated drive shaft, the threaded bone anchor relative to the implantation site in order to adance the anchor into the bone;

providing an elongated guide;

urging said elongated drive shaft relative to said guide in a direction to follow the threaded anchor into the bone to a predetermined depth;

providing a stop on said drive shaft to limit the longitudinal advancement of said drive shaft relative to said guide;

providing a first suture and a second suture, the diameter of said first suture being less than the diameter of said second suture;

passing both ends of said first suture through the eyelet of the anchor to thereby form a loop between the eyelet and the bight portion of the first suture;

passing one end of said second suture through tissue to be anchored by the anchor;

passing said one end of said second suture through the loop of said first suture;

pulling both ends of said first suture from said anchor in order to pull said one leg of said second suture through said eyelet.

* * * * *